United States Patent [19]

Sciavolino et al.

[11] 4,382,086
[45] May 3, 1983

[54] 9-DIHYDRO-11,12-KETAL DERIVATIVES OF ERYTHROMYCIN A AND EPI-ERYTHROMYCIN A

[75] Inventors: Frank C. Sciavolino, Niantic; James R. Hauske, East Lyme, both of Conn.

[73] Assignee: Pfizer Inc., New York, N.Y.

[21] Appl. No.: 353,548

[22] Filed: Mar. 1, 1982

[51] Int. Cl.³ .................... A61K 31/70; C07H 17/8
[52] U.S. Cl. .................................... 424/180; 536/7.2
[58] Field of Search .............. 424/180; 536/9, 7.2

[56] References Cited

U.S. PATENT DOCUMENTS

| | | | |
|---|---|---|---|
| 2,653,899 | 9/1953 | Bunch et al. | 167/65 |
| 3,417,077 | 12/1968 | Murphy et al. | 260/210 |
| 3,884,903 | 5/1975 | Jones et al. | 260/210 E |
| 4,150,220 | 4/1979 | Sciavolino | 536/9 |

OTHER PUBLICATIONS

K. Gerzon et al., and M. V. Sigal et al., J. Am. Chem. Soc., 78, 6396, (1956).

Primary Examiner—Johnnie R. Brown
Attorney, Agent, or Firm—Charles J. Knuth; Albert E. Frost; James M. McManus

[57] ABSTRACT

Antibacterial macrolides derived from 9-dihydro-11,12-O-isopropylidene-erythromycin A and 9-dihydro-11,12-O-isopropylidene-4″-epi-erythromycin A.

5 Claims, No Drawings

9-DIHYDRO-11,12-KETAL DERIVATIVES OF ERYTHROMYCIN A AND EPI-ERYTHROMYCIN A

FIELD OF THE INVENTION

This invention relates to novel semi-synthetic macrolide antibiotics and in particular to 9-dihydro-11,12-O-isopropylidene-erythromycin A and to 9-dihydro-11,12-O-isopropylidene-4''-epi erythromycin A derivatives.

DESCRIPTION OF THE ART

Erythromycin is an antibiotic formed during the culturing of a strain of Streptomyces erythreus in a suitable medium as taught in U.S. Pat. No. 2,653,899. Erythromycin, which is produced in two forms, A and B, is represented by the following structure:

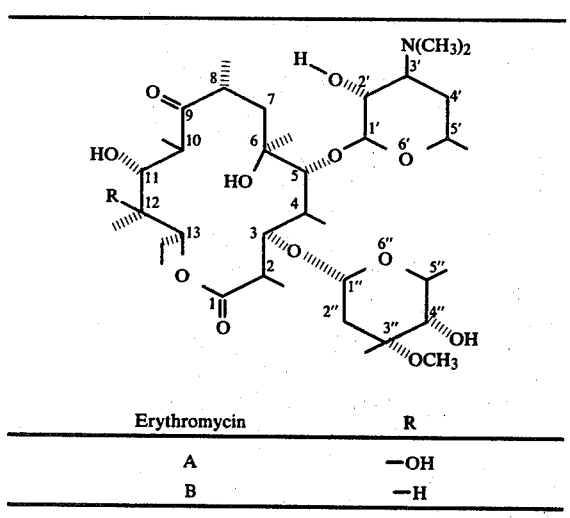

| Erythromycin | R |
|---|---|
| A | —OH |
| B | —H |

Numerous derivatives of erythromycin have been prepared in an effort to modify its biological or pharmacodynamic properties.

U.S. Pat. No. 3,417,077 describes the reaction product of erythromycin and ethylene carbonate as a very active antibacterial agent. U.S. Pat. No. 3,884,903 discloses 4''-deoxy-4''-oxo-erythromycin A and B derivatives as being useful as antibiotics, and U.S. Pat. No. 4,150,220 describes a new synthesis for 4''-oxo-erythromycin and its use as an intermediate leading to antibacterial agents.

9-Dihydroerythromycin A was reported by K. Gerzon, et al., *J. Am. Chem. Soc.*, 78, 6396 (1956) and M. V. Sigal, et al., *J. Am. Chem. Soc.*, 78, 388 (1956).

SUMMARY OF THE INVENTION

The semisynthetic macrolide antibacterial agents of the present invention are represented by the formula

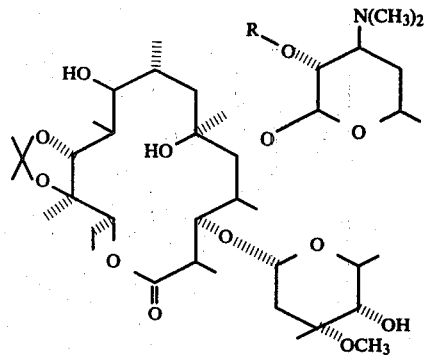

and the pharmaceutically acceptable acid addition salts thereof wherein R is alkanoyl having from two to three carbon atoms, hydrogen or ethyl succinyl.

A preferred group of compounds are those wherein R is hydrogen. Especially preferred within this group is the compound where the $C_{4''}$-hydroxyl group is axial and the compound where the $C_{4''}$-hydroxyl group is equatorial.

Also, within the scope of the present invention is a pharmaceutical composition comprising the compounds of the present invention with a pharmaceutically acceptable carrier and a method of treating an animal of diseases caused by Gram-positive bacteria which comprises administering to said animal an antibacterially effective amount of a compound of the present invention.

DETAILED DESCRIPTION OF THE INVENTION

The antibacterial compounds of the present invention having the natural conformation at $C_{4''}$ are synthesized by the following scheme, starting with 9-dihydroerythromycin A:

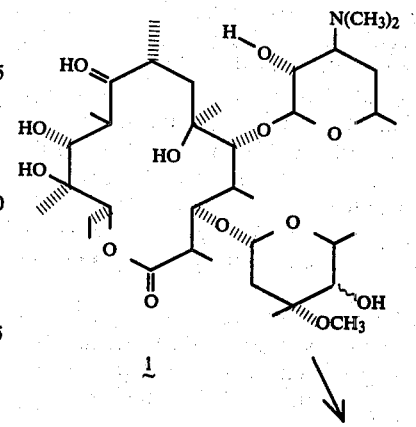

1

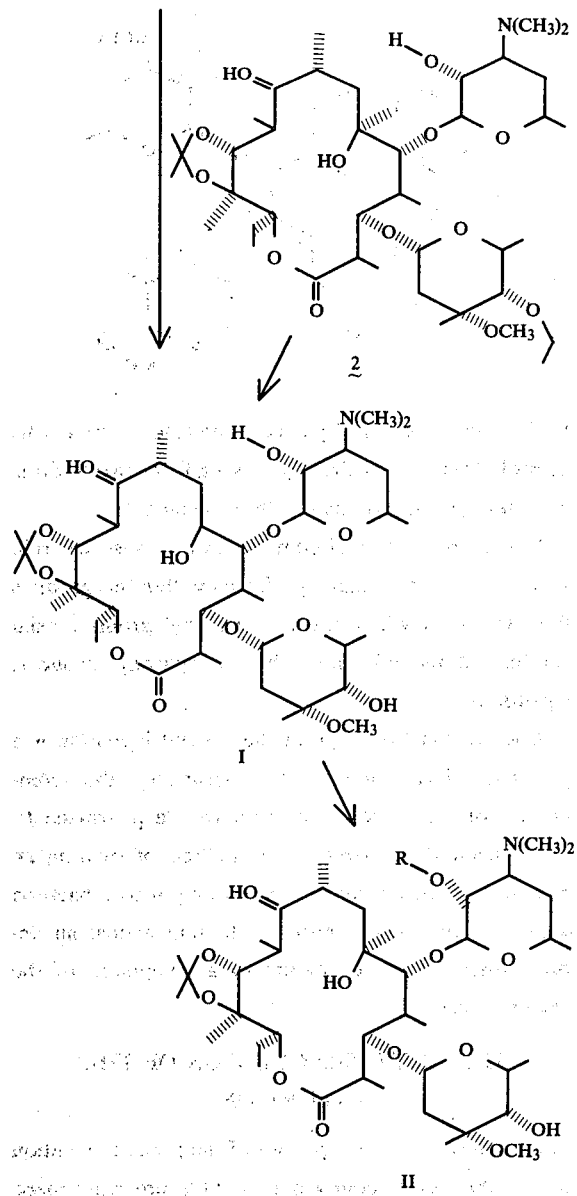

In practice, a mixture of 1 and 2-methoxypropene in a reaction-inert solvent is treated with pyridine hydrochloride at ambient temperatures, resulting in the formation of about a 1:1 mixture of I and 2. Conversion of 2 to I is achieved by acid hydrolysis without degradation of the 11,12-O-ketal structure, and without the separation of the initially formed I from 2.

The initial reaction is carried out using a ten-fold molar ratio of 2-methoxypropene per mole of 1. Lower amounts of the enol ether can be employed, but results in lower yields of I. Larger than ten-fold quantities of enol ether increases the amount of 2 formed. For each mole of 1 employed, approximately one mole plus as much as a one mole excess of pyridine hydrochloride is used.

It is preferred that the pyridine hydrochloride be added to 1 and 2-methoxypropene in the reaction-inert solvent at about ice-bath temperatures and the reaction mixture allowed to warm to room temperature. At ambient temperatures the reaction is finished in 6–10 hours, and can be conveniently carried out overnight.

As for the solvent in which the aforedescribed process can be conducted, a reaction-inert solvent is preferred. By such a solvent is meant one which solubilizes the appropriate reagents but does not react to any appreciable extent with either the starting reagents or final product. Solvents or mixtures thereof which are suitable include halogenated solvents such as chloroform and methylene chloride, aromatic solvents such as toluene, and ethers such as tetrahydrofuran and diethyl ether. The preferred solvent is chloroform.

On completion of the reaction the mixture is quenched with water at pH 9.5, and the products I and 2 are suspended in water-acetone at pH 3.6 in order to convert any 2 to I. This conversion requires stirring at the indicated pH for about 2 hours at room temperature. The pH is then made basic and the product I extracted with a water-immiscible solvent such as methylene chloride. Purification of the product is carried out by conventional means.

Preparation of compounds of formula II, wherein R is as defined, but other than hydrogen, is achieved by treatment of I with the appropriate anhydride or acid chloride.

When I is treated with an anhydride, one mole of I in a reaction-inert solvent is treated with at least one mole of the appropriate anhydride. In most instances it is preferred that as much as a fifty percent excess of the anhydride be employed to ensure completeness of reaction.

In practice, the anhydride is added to I at 0° C. and the resulting reaction mixture allowed to warm to room temperature. At ambient temperatures the reaction is complete in about 8–12 hours.

The reaction-inert solvent for the acylation reaction should have the same characteristics as previously defined. The preferred solvent is methylene chloride or acetone. On completion of the reaction the mixture is treated with water at pH 9.5 and the product extracted with a water immiscible solvent. Isolation and purification is by conventional means.

When an acid chloride is employed as the acylating agent, the reaction is conducted in essentially the same manner as when an anhydride is used. Accordingly, the acid chloride is added to I in a reaction-inert solvent at 0° C. and the reaction mixture is maintained at this temperature throughout the reaction period. Under these reaction conditions the acylation is complete in about 4–8 hours.

As in the case of acylation with an anhydride, it is preferred that an excess of acid chloride be employed to complete the reaction.

When using an acid chloride as the acylating agent sodium bicarbonate can be added as the acid scavenger for the hydrogen chloride formed. In such cases a molar amount equivalent to the macrolide plus an excess can be employed.

The resulting product is isolated and purified by the same procedure previously described when an anhydride is employed in synthesizing II.

The antibacterial compounds of the present invention having the unnatural conformation at $C_{4''}$ are synthesized by the following scheme, starting with 4''-deoxy-4''-oxoerythromycin A:

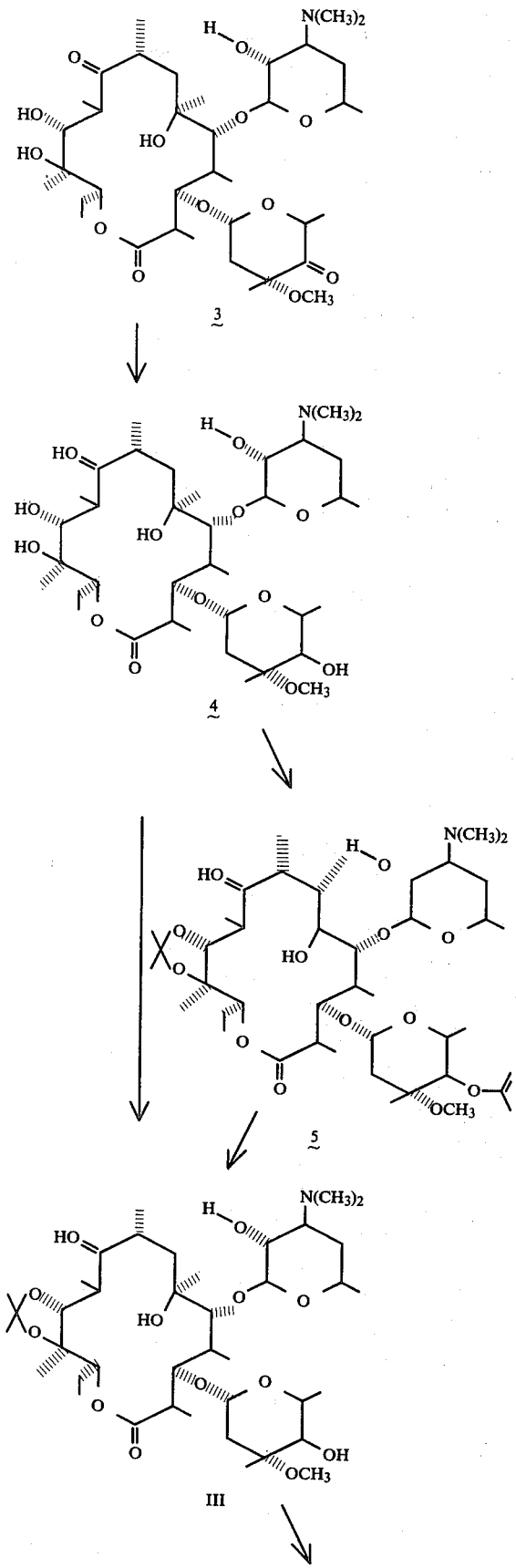

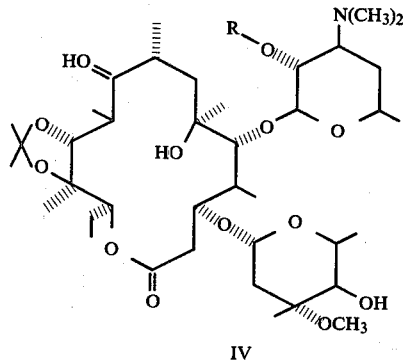

In practice, 3 is hydrogenated over a Raney nickel catalyst at about 1400 psi overnight to give 9-dihydro-4''-epi-erythromycin A, intermediate 4.

Intermediate 4 is reacted with 2-methoxypropene under the same experimental conditions previously discussed for 1, to give a mixture of the 11,12-O-ketal III as well as 5. Compound 5 is converted to III in exactly the same manner in which 2 was converted to I using an acid at pH about 3.5.

In addition, compounds of formula IV, the 2'-esters, are prepared in the same manner as that employed for compounds of formula II.

The reagents for the processes leading to the compounds of the present invention are known in the art. The preparation of 4''-deoxy-4''-oxo-erythromycin A is reported in U.S. Pat. No. 4,150,220 while the preparation of 9-dihydroerythromycin A is reported in *J. Am. Chem. Soc.*, 78, 388 (1956).

Preferred among the antibacterial compounds of the present invention are 9-dihydro-11,12-O-isopropylidene-erythromycin A and 9-dihydro-11,12-O-isopropylidene-4''-epi-erythromycin, these being the C4''-equatorial and axial isomers of 9-dihydro-11,12-O-isopropylidene-erythromycin A.

In the utilization of the chemotherapeutic activity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel erythromycins described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sickroom utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo such as *Pasteurella multocida, Hemophilus influenza,* and *Neisseria sicca* via the oral and/or parenteral routes of administration in animals, including man. Their in vivo activity is more limited as regards susceptible organisms and is determined by the usual procedure which comprises treating mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour postinoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 100 mg/kg to about 200 mg/kg of body weight per day. The favored dosage range is from about 150 mg/kg to about 200 mg/kg of body weight per day. Vehicles suitable for parenteral injection may be either aqueous such as water, isotonic saline, isotonic dextrose, Ringers' solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE I

9-Dihydro-11,12-O-isopropylidene-erythromycin A(I)

To a stirred suspension of 50 g (68 mmoles) of 9-dihydroerythromycin A and 64 ml (680 mmoles) of 2-methoxypropene in 1 liter of chloroform maintained at 0° C. was added portionwise 12 g (102 mmoles) of pyridine hydrochloride. The mixture was allowed to stir at room temperature overnight, and then poured into 1 liter of water and the pH adjusted to 9.5 with 6 N sodium hydroxide solution. The chloroform layer was separated and concentrated to dryness in vacuo. The solid residue was dissolved in acetone/water and the pH adjusted to 3.6 with 6 N hydrochloric acid. After stirring at room temperature for 2 hours the solution was poured into methylene chloride/water and the pH adjusted with 6 N sodium hydroxide solution. The organic layer was separated, dried over sodium sulfate and concentrated under vacuum to a colorless solid. The residue was purified by recrystallization from ethanol-water to give 38 g., m.p. 217.

The NMR spectrum (CDCl$_3$) showed absorption at 0.8–1.3 (41H, m), 1.4 (6H, s), 2.2 (6H, s), 3.3 (3H, s) and 3.4–5.1 (13H, m) ppm.

Analysis: Calc'd for $C_{40}H_{73}NO_{13}$: C, 61.91; H, 9.48; N, 1.81. Found: C, 61.97; H, 9.20; N, 1.75. $[\alpha]_D^{22}$ (CHCl$_3$, 1% w/v) = −36.1°

EXAMPLE II

General Procedure for 2'-Ester Preparation via Anhydride

To a methylene chloride solution (10%) of one equivalent of 9-dihydro-11,12-O-isopropylidene-erythromycin A maintained at 0° C. was added dropwise 1.5 equivalents of the appropriate anhydride. The reaction mixture was allowed to warm to room temperature and was stirred at ambient temperatures for 12 hours. The reaction mixture was then poured into water/methylene chloride and the pH adjusted to 9.5 with 6 N sodium hydroxide solution. The organic layer was separated, dried over sodium sulfate and concentrated in vacuo. The product was recrystallized from acetone-water.

Using the above procedure was prepared:

9-dihydro-11,12-O-isopropylidene-2'-acetyl-erythromycin A, m.p. 182°–184° C. The NMR spectrum (CDCl$_3$) showed absorption at 0.8–1.3 (41H, m), 1.4 (6H, s), 2.1 (6H, s), 3.3 (3H, s) and 3.4–5.1 (12H, m) ppm.

9-dihydro-11,12-O-isopropylidene-2'-propionyl-erythromycin A, m.p. 189°–191° C. The NMR spectrum (CDCl$_3$) showed absorption at 0.8–1.3 (46H, m), 1.4 (6H, s), 2.1–2.3(2H, m), 3.4 (3H, s) and 3.4–5.1 (12H, m) ppm.

EXAMPLE III

9-Dihydro-11,12-O-isopropylidene-2'-(ethyl succinyl)erythromycin A

To a solution of 1.82 g (2.5 mmoles) of 9-dihydro-11,12-O-isopropylidene-erythromycin A in 25 ml of methylene chloride cooled to 0° C. was added dropwise 0.92 ml (6.5 mmoles) of ethyl succinyl chloride and the mixture allowed to stir at 0° C. for 4 hours. The reaction mixture was poured into methylene chloride/water and the pH adjusted to 9.5 with 6 N sodium hydroxide solution. The organic layer was separated, dried over sodium sulfate and concentrated to dryness in vacuo. The residual product was recrystallized from acetone/water to give 1.0 g., m.p. 169°–170° C.

The NMR spectrum (CDCl$_3$) showed absorption at 0.8–1.3 (41H, m), 1.4 (6H, s), 2.2 (6H, s), 2.6 (4H, m), 3.3 (3H, s), 4.1 (2H, m), and 4.4–5.1 (10H, m) ppm.

In a similar manner, starting with 9-dihydro-11,12-O-isopropylidene-erythromycin A and the appropriate acid chloride are prepared 9-dihydro-11,12-O-isopropylidene-2'-acetyl-erythromycin and 9-dihydro-11,12-O-isopropylidene-2'-propionyl-erythromycin A.

EXAMPLE IV

9-Dihydro-4''-epi-erythromycin A

A slurry of 50 g (68.3 mmoles) of 4''-deoxy-4''-oxo-erythromycin A and 250 g of Raney nickel was shaken in a hydrogen atmosphere at an initial pressure of 1400 psi at room temperature overnight. The mixture was filtered through super-cel and the filtrate concentrated under vacuum to a colorless solid, which was purified by recrystallization from acetone/water, 40 g., m.p. 139°–143° C.

EXAMPLE V

9-Dihydro-11,12-O-isopropylidene-4''-epi-erythromycin A

To a chloroform solution (700 ml) of 65 g (88.3 mmoles) of 9-dihydro-4''-epi-erythromycin A and 82.6 ml (883 mmoles) of 2-methoxypropene maintained at 0° C. was added portionwise 15.3 g (132 mmoles) of pyridine hydrochloride. The reaction was allowed to warm to room temperature and was stirred at ambient temperatures overnight. The reaction mixture was poured into water and the pH adjusted to 9.5 with 6 N sodium hydroxide. The organic layer was separated, dried over sodium sulfate and concentrated in vacuo to give a colorless solid. The residual solid was dissolved in acetone/water and the pH adjusted to 3.5 with 6 N hydrochloric acid. After about 2 hours the pH of the solution was raised to 6.2 with 6 N sodium hydroxide and the solution treated with charcoal and filtered. The filtrate was poured into a mixture of chloroform/water and the pH raised further to 9.5 with 6 N sodium hydroxide solution. The organic layer was separated, dried over sodium sulfate and concentrated to dryness. The residual solid was recrystallized from ethanol/water to give 50 g of the product, m.p. 214°–217° C.

The NMR spectrum (CDCl$_3$) showed absorption at 0.8–1.3 (41H, m), 1.4 (6H, s), 2.2 (6H, s), 3.3 (3H, s), and 3.5–5.1 (13H, m) ppm.

Analysis: Calc'd for C$_{40}$H$_{73}$NO$_{13}$: C, 61.91; H, 9.48; N, 1.81. Found: C, 61.96; H, 9.51; N, 1.86. [alpha]$_D^{22}$ (CHCl$_3$, 1% w/v) = −35.9°

EXAMPLE VI

9-Dihydro-11,12-O-isopropylidene-2'-acetyl-4''-epi-erythromycin A

To a solution of 1.25 g (1.6 mmoles) of 9-dihydro-11,12-O-isopropylidene-4''-epi-erythromycin A in 12 ml of methylene chloride was added 0.167 ml (1.77 mmoles) of acetic anhydride and the resulting mixture allowed to stir at room temperature overnight. The reaction mixture was poured into water and the pH adjusted to 9.5 with 6 N sodium hydroxide solution. The organic phase was separated, dried over sodium sulfate and concentrated under vacuum to give a colorless solid. The residue was recrystallized from diethyl ether, 1.0 g, m.p. 138°–142° C.

The NMR spectrum (CDCl$_3$) showed absorption at 0.8–1.3 (41H, m), 1.4 (6H, s), 2.0 (3H, s), 2.2 (6H, s), and 3.4 (3H, s) ppm.

In a similar manner, starting with 1.3 g of 9-dihydro-11,12-O-isopropylidene-4''-epi-erythromycin A and 0.236 ml of propionic anhydride, there was obtained 0.90 g of 9-dihydro-11,12-O-isopropylidene-2'-propionyl-4''-epi-erythromycin A, m.p. 128°–133° C.

The NMR spectrum (CDCl$_3$) showed absorption at 0.8–1.3 (H, m), 1.4 (6H, s), 2.3 (6H, s) and 3.4 (3H, s) ppm.

EXAMPLE VII

9-Dihydro-11,12-O-isopropylidene-2'-(ethyl succinyl)-4''-epi-erythromycin A

To an acetone solution (12 ml) of 9-dihydro-11,12-O-isopropylidene-4''-epi-erythromycin A (1.2 g, 1.55 mmoles) and sodium bicarbonate (800 mg) was added 0.242 ml (1.7 mmoles) of ethyl succinyl chloride and the mixture allowed to stir at room temperature overnight. An additional 66.2 μl (0.465 mmole) of the acid chloride was added and the reaction allowed to continue for 2 hours. The mixture was then poured into methylene chloride and water. The organic phase was separated, dried over sodium sulfate and concentrated to give 0.90 g of the product.

The NMR spectrum (CDCl$_3$) showed absorption at 0.8–1.3 (41H, m), 1.4 (6H, s), 2.3 (6H, s), 2.6 (4H, s), 3.4 (3H, s) and 4.1 (2H, q) ppm.

In a similar manner, by replacing ethyl succinyl chloride with acetyl chloride and propionyl chloride, 9-dihydro-11,12-O-isopropylidene-2'-acetyl-4''-epi-erythromycin A and 9-dihydro-11,12-O-isopropylidene-2'-propionyl-4''-epi-erythromycin A are prepared, respectively.

We claim:

1. A compound selected from the group consisting of a macrolide of the formula:

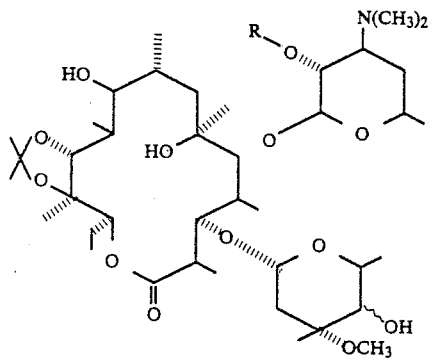

and the pharmaceutically acceptable acid addition salts thereof, wherein R is selected from the group consisting of hydrogen, alkanoyl having two to three carbon atoms and ethyl succinyl.

2. A compound of claim 1, wherein R is hydrogen.

3. The compound of claim 2, wherein the C$_{4''}$-hydroxyl group is axial.

4. The compound of claim 2, wherein the C$_{4''}$-hydroxyl group is equatorial.

5. An antibacterial pharmaceutical composition comprising from about 0.5 to about 90 percent by weight of the total composition a compound as claimed in claim 1 and a pharmaceutically acceptable carrier.

* * * * *